(12) United States Patent
Sakai et al.

(10) Patent No.: US 11,225,644 B2
(45) Date of Patent: Jan. 18, 2022

(54) CELL CULTURE METHOD, CELL AGGREGATES, CELL AGGREGATION CONTROL AGENT, AND MEDIUM

(71) Applicants: THE UNIVERSITY OF TOKYO, Tokyo (JP); SOMAR CORPORATION, Tokyo (JP)

(72) Inventors: Yasuyuki Sakai, Tokyo (JP); Ikki Horiguchi, Tokyo (JP); Kumiko Matsunaga, Tokyo (JP); Shunji Hayasaka, Tokyo (JP)

(73) Assignees: SOMAR CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 56 days.

(21) Appl. No.: 15/547,316

(22) PCT Filed: Jan. 27, 2016

(86) PCT No.: PCT/JP2016/052398
§ 371 (c)(1),
(2) Date: Jul. 28, 2017

(87) PCT Pub. No.: WO2016/121840
PCT Pub. Date: Aug. 4, 2016

(65) Prior Publication Data
US 2018/0023057 A1   Jan. 25, 2018

(30) Foreign Application Priority Data

Jan. 29, 2015  (JP) .............................. JP2015-016045

(51) Int. Cl.
*C12N 5/074* (2010.01)
*C12N 5/10* (2006.01)
(Continued)

(52) U.S. Cl.
CPC .............. *C12N 5/0696* (2013.01); *C07K 2/00* (2013.01); *C07K 14/70596* (2013.01);
(Continued)

(58) Field of Classification Search
None
See application file for complete search history.

(56) References Cited

U.S. PATENT DOCUMENTS

2004/0214333 A1   10/2004   Liu et al.
2004/0265996 A1   12/2004   Schwarz et al.
(Continued)

FOREIGN PATENT DOCUMENTS

JP   2004-536606 A   12/2004
JP   2006-518219 A   8/2006
(Continued)

OTHER PUBLICATIONS

Rodin et al., Nature Comm. 5: 3195 (2014).*
(Continued)

*Primary Examiner* — Erin M. Bowers
(74) *Attorney, Agent, or Firm* — Birch, Stewart, Kolasch & Birch, LLP

(57) ABSTRACT

A method for culturing cells by which the diameter of cell aggregates can be controlled, and by which a large amount of cells can be obtained, a cell aggregate obtained by the method, a cell aggregation control agent, and a medium containing the cell aggregation control agent, are provided. A method for culturing cells by suspension culture, which method includes an aggregation control step of adding a substance that inhibits a cell adhesion molecule(s) of the cells to a medium to control cell aggregation of the cells, and the like are provided.

6 Claims, 7 Drawing Sheets

Specification includes a Sequence Listing.

(51) Int. Cl.
  *C07K 2/00* (2006.01)
  *C07K 16/18* (2006.01)
  *C07K 14/78* (2006.01)
  *C07K 19/00* (2006.01)
  *C07K 14/705* (2006.01)

(52) U.S. Cl.
  CPC .............. *C07K 14/78* (2013.01); *C07K 16/18* (2013.01); *C07K 19/00* (2013.01); *C12N 5/10* (2013.01); *C07K 2319/30* (2013.01); *C12N 2501/599* (2013.01)

(56) References Cited

U.S. PATENT DOCUMENTS

| | | |
|---|---|---|
| 2007/0155013 A1 | 7/2007 | Akaike et al. |
| 2010/0240066 A1 | 9/2010 | Blaschuk et al. |
| 2012/0058561 A1 | 3/2012 | Sato |
| 2014/0011275 A1 | 1/2014 | Lee et al. |
| 2014/0113372 A1 | 4/2014 | Haque et al. |
| 2015/0118194 A1 | 4/2015 | Ra et al. |
| 2015/0329831 A1 | 11/2015 | Kinooka et al. |
| 2017/0130206 A1 | 5/2017 | Kinooka et al. |

FOREIGN PATENT DOCUMENTS

| | | |
|---|---|---|
| JP | 2011-103882 A | 6/2011 |
| JP | 2012-523240 A | 10/2012 |
| JP | 2013-126405 A | 6/2013 |
| JP | 2014-82956 A | 5/2014 |
| JP | 2016-28567 A | 3/2016 |
| WO | WO 2005/090557 A1 | 9/2005 |
| WO | WO 2006/116737 A2 | 11/2006 |
| WO | WO 2007/088372 * | 8/2007 |
| WO | WO 2013/154404 A1 | 10/2013 |
| WO | WO 2014/072720 A2 | 5/2014 |
| WO | WO 2014/104207 A1 | 7/2014 |
| WO | WO 2015/199243 A1 | 12/2015 |

OTHER PUBLICATIONS

Sajini et al., Dev. Biol. 371: 170-179 (2012).*
International Search Report for PCT/JP2016/052398 (PCT/ISA/210) dated Apr. 5, 2016.
Olmer et al., "Suspension Culture of Human Pluripotent Stem Cells in Controlled, Stirred Bioreactors", Tissue Engineering: Part C, vol. 18, No. 10, 2012, pp. 1-13.
Otsuji et al., "A 3D Sphere Culture System Containing Functional Polymers for Large-Scale Human Pluripotent Stem Cell Production", Stem Cell Reports, vol. 2, May 6, 2014, pp. 734-745.
Schroeder et al., "Differentiation and Lineage Selection of Mouse Embryonic Stem Cells in a Stirred Bench Scale Bioreactor With Automated Process Control", Biotechnology and Bioengineering, vol. 2, No. 7, Dec. 30, 2005, pp. 920-933.
Written Opinion of the International Searching Authority for for PCT/JP2016/052398 (PCT/ISA/237) dated Apr. 5, 2016.
Extended European Search Report, dated Jul. 24, 2018, for European Application No. 16743443.0.
Mohamet et al., "Abrogation of E-Cadherin-Mediated Cellular Aggregation Allows Proliferation of Pluripotent Mouse Embryonic Stem Cells in Shake Flask Bioreactors," PLoS One, vol. 5, No. 9, e12921, Sep. 2010, 12 pages total.

* cited by examiner

```
                        SEQUENCE LISTING

<160> NUMBER OF SEQ ID NOS: 30

<210> SEQ ID NO 1
<211> LENGTH: 882
<212> TYPE: PRT
<213> ORGANISM: Human

<400> SEQUENCE: 1

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro Pro His
            115                 120                 125

Gln Ala Ser Val Ser Gly Ile Gln Ala Glu Leu Leu Thr Phe Pro Asn
        130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285
```

-continued

```
Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700
```

-continued

Leu Gln Ile Pro Ala Ile Gly Ile Gly Gly Ile Leu Ala Leu
705                 710                 715                 720

Leu Ile Leu Ile Leu Leu Leu Leu Phe Leu Arg Arg Arg Ala Val
            725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
            755                 760                 765

Leu Ser Gln Leu His Arg Gly Leu Asp Ala Arg Pro Glu Val Thr Arg
770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
            835                 840                 845

Asn Ser Ser Glu Ser Asp Lys Asp Gln Asp Tyr Asp Tyr Leu Asn Glu
850                 855                 860

Trp Gly Asn Arg Phe Lys Lys Leu Ala Asp Met Tyr Gly Gly Gly Glu
865                 870                 875                 880

Asp Asp

<210> SEQ ID NO 2
<211> LENGTH: 884
<212> TYPE: PRT
<213> ORGANISM: Mouse

<400> SEQUENCE: 2

Met Gly Ala Arg Cys Arg Ser Phe Ser Ala Leu Leu Leu Leu Gln
1               5                   10                  15

Val Ser Ser Trp Leu Cys Gln Glu Leu Glu Pro Glu Ser Cys Ser Pro
            20                  25                  30

Gly Phe Ser Ser Glu Val Tyr Thr Phe Pro Val Pro Glu Arg His Leu
        35                  40                  45

Glu Arg Gly His Val Leu Gly Arg Val Arg Phe Glu Gly Cys Thr Gly
    50                  55                  60

Arg Pro Arg Thr Ala Phe Phe Ser Glu Asp Ser Arg Phe Lys Val Ala
65                  70                  75                  80

Thr Asp Gly Thr Ile Thr Val Lys Arg His Leu Lys Leu His Lys Leu
                85                  90                  95

Glu Thr Ser Phe Leu Val Arg Ala Arg Asp Ser Ser His Arg Glu Leu
            100                 105                 110

Ser Thr Lys Val Thr Leu Lys Ser Met Gly His His His Arg His
        115                 120                 125

His His Arg Asp Pro Ala Ser Glu Ser Asn Pro Glu Leu Leu Met Phe
130                 135                 140

Pro Ser Val Tyr Pro Gly Leu Arg Arg Gln Lys Arg Asp Trp Val Ile
145                 150                 155                 160

Pro Pro Ile Ser Cys Pro Glu Asn Glu Lys Gly Glu Phe Pro Lys Asn
                165                 170                 175

Leu Val Gln Ile Lys Ser Asn Arg Asp Lys Glu Thr Lys Val Phe Tyr
            180                 185                 190

-continued

```
Ser Ile Thr Gly Gln Gly Ala Asp Lys Pro Val Gly Val Phe Ile
        195                 200                 205
Ile Glu Arg Glu Thr Gly Trp Leu Lys Val Thr Gln Pro Leu Asp Arg
210                 215                 220
Glu Ala Ile Ala Lys Tyr Ile Leu Tyr Ser His Ala Val Ser Ser Asn
225                 230                 235                 240
Gly Glu Ala Val Glu Asp Pro Met Glu Ile Val Thr Val Thr Asp
                245                 250                 255
Gln Asn Asp Asn Arg Pro Glu Phe Thr Gln Pro Val Phe Glu Gly Phe
                260                 265                 270
Val Ala Glu Gly Ala Val Pro Gly Thr Ser Val Met Lys Val Ser Ala
                275                 280                 285
Thr Asp Ala Asp Asp Val Asn Thr Tyr Asn Ala Ala Ile Ala Tyr
290                 295                 300
Thr Ile Val Ser Gln Asp Pro Glu Leu Pro His Lys Asn Met Phe Thr
305                 310                 315                 320
Val Asn Arg Asp Thr Gly Val Ile Ser Val Leu Thr Ser Gly Leu Asp
                325                 330                 335
Arg Glu Ser Tyr Pro Thr Tyr Thr Leu Val Val Gln Ala Ala Asp Leu
                340                 345                 350
Gln Gly Glu Gly Leu Ser Thr Thr Ala Lys Ala Val Ile Thr Val Lys
                355                 360                 365
Asp Ile Asn Asp Asn Ala Pro Val Phe Asn Pro Ser Thr Tyr Gln Gly
        370                 375                 380
Gln Val Pro Glu Asn Glu Val Asn Ala Arg Ile Ala Thr Leu Lys Val
385                 390                 395                 400
Thr Asp Asp Asp Ala Pro Asn Thr Pro Ala Trp Lys Ala Val Tyr Thr
                405                 410                 415
Val Val Asn Asp Pro Asp Gln Gln Phe Val Val Thr Asp Pro Thr
                420                 425                 430
Thr Asn Asp Gly Ile Leu Lys Thr Ala Lys Gly Leu Asp Phe Glu Ala
        435                 440                 445
Lys Gln Gln Tyr Ile Leu His Val Arg Val Glu Asn Glu Glu Pro Phe
450                 455                 460
Glu Gly Ser Leu Val Pro Ser Thr Ala Thr Val Thr Val Asp Val Val
465                 470                 475                 480
Asp Val Asn Glu Ala Pro Ile Phe Met Pro Ala Glu Arg Arg Val Glu
                485                 490                 495
Val Pro Glu Asp Phe Gly Val Gly Gln Glu Ile Thr Ser Tyr Thr Ala
                500                 505                 510
Arg Glu Pro Asp Thr Phe Met Asp Gln Lys Ile Thr Tyr Arg Ile Trp
        515                 520                 525
Arg Asp Thr Ala Asn Trp Leu Glu Ile Asn Pro Glu Thr Gly Ala Ile
        530                 535                 540
Phe Thr Arg Ala Glu Met Asp Arg Glu Asp Ala Glu His Val Lys Asn
545                 550                 555                 560
Ser Thr Tyr Val Ala Leu Ile Ile Ala Thr Asp Asp Gly Ser Pro Ile
                565                 570                 575
Ala Thr Gly Thr Gly Thr Leu Leu Leu Val Leu Leu Asp Val Asn Asp
                580                 585                 590
Asn Ala Pro Ile Pro Glu Pro Arg Asn Met Gln Phe Cys Gln Arg Asn
        595                 600                 605
Pro Gln Pro His Ile Ile Thr Ile Leu Asp Pro Asp Leu Pro Pro Asn
```

```
                610                 615                 620
Thr Ser Pro Phe Thr Ala Glu Leu Thr His Gly Ala Ser Val Asn Trp
625                 630                 635                 640

Thr Ile Glu Tyr Asn Asp Ala Ala Gln Glu Ser Leu Ile Leu Gln Pro
                645                 650                 655

Arg Lys Asp Leu Glu Ile Gly Glu Tyr Lys Ile His Leu Lys Leu Ala
            660                 665                 670

Asp Asn Gln Asn Lys Asp Gln Val Thr Thr Leu Asp Val His Val Cys
        675                 680                 685

Asp Cys Glu Gly Thr Val Asn Asn Cys Met Lys Ala Gly Ile Val Ala
    690                 695                 700

Ala Gly Leu Gln Val Pro Ala Ile Leu Gly Ile Leu Gly Gly Ile Leu
705                 710                 715                 720

Ala Leu Leu Ile Leu Ile Leu Leu Leu Leu Phe Leu Arg Arg Arg
                725                 730                 735

Thr Val Val Lys Glu Pro Leu Leu Pro Pro Asp Asp Asp Thr Arg Asp
                740                 745                 750

Asn Val Tyr Tyr Tyr Asp Glu Glu Gly Gly Gly Glu Glu Asp Gln Asp
                755                 760                 765

Phe Asp Leu Ser Gln Leu His Arg Gly Leu Asp Ala Arg Pro Glu Val
770                 775                 780

Thr Arg Asn Asp Val Ala Pro Thr Leu Met Ser Val Pro Gln Tyr Arg
785                 790                 795                 800

Pro Arg Pro Ala Asn Pro Asp Glu Ile Gly Asn Phe Ile Asp Glu Asn
                805                 810                 815

Leu Lys Ala Ala Asp Ser Asp Pro Thr Ala Pro Pro Tyr Asp Ser Leu
                820                 825                 830

Leu Val Phe Asp Tyr Glu Gly Ser Gly Ser Glu Ala Ala Ser Leu Ser
                835                 840                 845

Ser Leu Asn Ser Ser Glu Ser Asp Gln Asp Gln Asp Tyr Asp Tyr Leu
                850                 855                 860

Asn Glu Trp Gly Asn Arg Phe Lys Lys Leu Ala Asp Met Tyr Gly Gly
865                 870                 875                 880

Gly Glu Asp Asp

<210> SEQ ID NO 3
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 3

Ser Trp Glu Leu Tyr Tyr Pro Leu Arg Ala Asn Leu
1               5                   10

<210> SEQ ID NO 4
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 4

Glu Trp Met Ile His Tyr Asp Ser Ala Leu Thr Ser
1               5                   10
```

```
<210> SEQ ID NO 5
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 5

Ala Trp Gln Val His Tyr Ser Tyr Val Ala Ser Ser
1               5                   10

<210> SEQ ID NO 6
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 6

Ser Trp Leu Ala Val Trp Pro Ala Thr Gly Ala Ser
1               5                   10

<210> SEQ ID NO 7
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 7

Trp Thr Met Cys Tyr Pro Asp Thr Cys
1               5

<210> SEQ ID NO 8
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 8

Trp Gln Phe Cys Tyr Ala Gln His Cys
1               5

<210> SEQ ID NO 9
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 9

Trp Gln Met Val Leu Cys Pro Ala Cys
1               5

<210> SEQ ID NO 10
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 10

Trp Glu Leu Val Gln Cys Leu Thr Cys
1               5

<210> SEQ ID NO 11
```

```
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 11

Trp Gln Trp Cys Phe Lys Ala Thr Cys
1               5

<210> SEQ ID NO 12
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 12

Trp Thr Phe Asn Phe Cys Thr Ala Cys
1               5

<210> SEQ ID NO 13
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 13

Trp Thr Trp His Trp Pro Pro Cys Cys
1               5

<210> SEQ ID NO 14
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 14

Cys Ser Lys Tyr Asn Ser Pro Leu Cys
1               5

<210> SEQ ID NO 15
<211> LENGTH: 9
<212> TYPE: PRT
<213> ORGANISM: Artificial
<220> FEATURE:
<223> OTHER INFORMATION: Peptide capable of binding to E-cadherin

<400> SEQUENCE: 15

Cys Ser Arg Pro Gln Ser Gly Leu Cys
1               5

<210> SEQ ID NO 16
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 16

Ser Trp Thr Trp His Phe Pro Glu Ser Pro Pro Pro
1               5                   10

<210> SEQ ID NO 17
<211> LENGTH: 12
```

```
<212> TYPE: PRT
<213> ORGANISM: Artificial
<220> FEATURE:
<223> OTHER INFORMATION: Peptide capable of binding to E-cadherin

<400> SEQUENCE: 17

Ser Trp Thr Phe Tyr Trp Pro Asp Ala Gln Leu Gly
1               5                   10

<210> SEQ ID NO 18
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 18

Glu Trp Thr Trp Val Phe Pro Thr Thr His Thr Ser
1               5                   10

<210> SEQ ID NO 19
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 19

Glu Trp Asp Phe Phe Trp Pro Pro Thr Gln Thr Pro
1               5                   10

<210> SEQ ID NO 20
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 20

Glu Trp Gln Tyr His Trp Pro Thr Leu Gln Ser Arg
1               5                   10

<210> SEQ ID NO 21
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 21

Gln Trp Gln Leu His Trp Pro Ala Ser Lys Gln Ala
1               5                   10

<210> SEQ ID NO 22
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 22

Gln Trp Thr Ile Thr Tyr Pro Lys Pro Pro Ala Leu
1               5                   10

<210> SEQ ID NO 23
<211> LENGTH: 12
<212> TYPE: PRT
```

```
<213> ORGANISM: Artificial
<220> FEATURE:
<223> OTHER INFORMATION: Peptide capable of binding to E-cadherin

<400> SEQUENCE: 23

Gly Trp Thr Val Phe Tyr Pro Asp Asn Leu Arg Pro
1               5                   10

<210> SEQ ID NO 24
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 24

Gln Trp Glu Trp His Tyr Met Ala Gly Tyr Leu Ala
1               5                   10

<210> SEQ ID NO 25
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 25

Gln Trp Glu Ile Arg Tyr Pro Trp Pro Ser Met Gly
1               5                   10

<210> SEQ ID NO 26
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 26

Gln Trp Thr Tyr Tyr Leu Pro Leu Thr Pro Arg Trp
1               5                   10

<210> SEQ ID NO 27
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 27

Glu Trp Thr Tyr Thr Phe Pro Thr Ala His Ser Ile
1               5                   10

<210> SEQ ID NO 28
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 28

Glu Trp Phe Trp Ser Trp Pro Gly Tyr Ser Asn Thr
1               5                   10

<210> SEQ ID NO 29
<211> LENGTH: 11
<212> TYPE: PRT
<213> ORGANISM: Artificial
```

```
<220> FEATURE:
<223> OTHER INFORMATION: Peptide capable of binding to E-cadherin

<400> SEQUENCE: 29

Ser Trp Glu Trp Ile Pro Tyr Leu Asn Arg Thr
1               5                   10

<210> SEQ ID NO 30
<211> LENGTH: 12
<212> TYPE: PRT
<213> ORGANISM: Artificial
<220> FEATURE:
<223> OTHER INFORMATION: Peptide capable of binding to E-cadherin

<400> SEQUENCE: 30

Ala Trp Thr Trp Ser Leu Pro Thr Leu Pro Gln Ser
1               5                   10
```

CELL CULTURE METHOD, CELL AGGREGATES, CELL AGGREGATION CONTROL AGENT, AND MEDIUM

TECHNICAL FIELD

The present invention relates to a method for culturing cells, a cell aggregate, a cell aggregation control agent, and a medium, more specifically, to a method for culturing cells by which the diameter of cell aggregates can be controlled, and by which a large amount of cells can be obtained, a cell aggregate obtained by the method, a cell aggregation control agent, and a medium containing the cell aggregation control agent.

BACKGROUND ART

Human liver is usually constituted by about 250 billion cells. Based on the assumption that about 10% of the original liver is required for producing a liver tissue using pluripotent stem cells, the number of cells required is about 25 billion. Since tests in drug trials require cells having a uniform quality (hereinafter also referred to as "homogeneous" cells), a technique that enables culture of a large amount of uniform pluripotent stem cells is an indispensable process for industrial application and development. With such a background, suspension culture methods have been proposed since they enable simple high-density culture for the purpose of stably supplying a large amount of pluripotent stem cells. This culture method is a culture method which is expected to enable production of cells in a number that allows their application to regenerative medicine and the like, and this method is advantageous from the viewpoint of the facility and the cost.

However, since pluripotent stem cells easily form aggregates, various aggregates such as huge aggregates and aggregates having uneven diameters are formed. There is also a problem that such aggregates show low cell survival rates after subculture. In view of this, three-dimensional suspension culture, in which a stirring operation using a spinner flask or the like is carried out for preventing precipitation of cells and cell clusters in the culture vessel, has been proposed (see Non-patent Document 1 and Non-patent Document 2). However, since pluripotent stem cells are sensitive to mechanical stresses caused by the stirring operation, the cells may be damaged during the culture, leading to deterioration of the quality due to the stresses, which is problematic.

Recently, in view of this, a process in which a medium, methyl cellulose, and gellan gum are contained in a culture bag, and pluripotent stem cells are cultured therein while pluripotent stem cell spheres are decomposed using a nylon mesh filter upon subculture has been proposed (see Non-patent Document 3). However, this method was not satisfactory from the viewpoint of the number of cells obtained. Further, since the viscosity of the culture liquid is increased with gellan gum for prevention of precipitation of cells and cell clusters, the stirring cannot even allow supply of nutrients and oxygen in the amounts at least required for the growth of the cells, so that, in cases where large cell clusters are formed, the cells in the inner side cannot survive, resulting in deterioration of the quality of the cells, which is problematic. Further, in cases where an increase in the size of cell clusters is inhibited in an attempt to allow survival of all cells in the resulting cell clusters, the number of cells obtained is small, which is problematic. Thus, the stem cells obtained by this culture method failed to satisfy both the cell quality and the number of cells obtained at the same time.

RELATED ART DOCUMENTS

Non Patent Documents

Non-patent Document 1: BIOTECHNOLOGY AND BIOENGINEERING, Vol. 92, NO. 7, 920 to 933, Dec. 30, 2005
Non-patent Document 2: TISSUE ENGINEERING: Part C Vol. 18, NO. 10, 1 to 13, 2012
Non-patent Document 3: Stem Cell Reports, Vol. 2, 734 to 745, May 6, 2014

SUMMARY OF THE INVENTION

Problems to be Solved by the Invention

In view of this, an object of the present invention is to provide a method for culturing cells by which the diameter of cell aggregates can be controlled, and by which a large amount of cells can be obtained, a cell aggregate obtained by the method, a cell aggregation control agent, and a medium containing the cell aggregation control agent.

Means for Solving the Problems

As a result of intensive study, the present inventors discovered that, by inclusion of a substance that inhibits a cell adhesion molecule(s) in the medium, the function of the cell adhesion molecule(s) involved in formation of aggregates can be controlled, and that, by controlling the diameter of the aggregates in suspension culture by this, the above problem can be solved, thereby completing the present invention.

That is, the present invention is the following [1] to [11], which relate to a method for culturing cells, a cell aggregate, a cell aggregation control agent, and a medium.
[1] A method for culturing cells by suspension culture, the method comprising an aggregation control step of adding a substance that inhibits a cell adhesion molecule(s) of the cells to a medium to control cell aggregation of the cells.
[2] The culture method according to [1], wherein, in the aggregation control step, the substance that inhibits a cell adhesion molecule(s) is added to the medium at a concentration of 10 to 50 µg/ml.
[3] The culture method according to [1] or [2], wherein the substance that inhibits a cell adhesion molecule(s) is at least one selected from cell adhesion molecules, proteins composed of partial regions of cell adhesion molecules, fusion proteins containing the whole or partial regions of cell adhesion molecules, neutralizing antibodies against cell adhesion molecules, peptides that bind to cell adhesion molecules, and derivatives thereof.
[4] The culture method according to any one of [1] to [3], wherein the substance that inhibits a cell adhesion molecule(s) contains at least one selected from E-cadherin, proteins composed of partial regions of E-cadherin, fusion proteins containing the whole or a partial region of E-cadherin, neutralizing antibodies against E-cadherin, peptides that bind to E-cadherin, and derivatives thereof.
[5] The culture method according to any one of [1] to [4], wherein the cells are stem cells or epithelial cells.
[6] An aggregate of the cells obtained by the culture method according to any one of [1] to [5], having a uniform aggregation diameter.

[7] The aggregate according to [6], wherein the diameter of the aggregate after 48 hours of suspension culture is not less than 20 μm and less than 1 mm.
[8] A cell aggregation control agent comprising a substance that inhibits a cell adhesion molecule(s).
[9] The cell aggregation control agent according to [8], comprising, as the substance that inhibits a cell adhesion molecule(s), at least one selected from E-cadherin, proteins composed of partial regions of E-cadherin, fusion proteins containing the whole or a partial region of E-cadherin, neutralizing antibodies against E-cadherin, peptides that bind to E-cadherin, and derivatives thereof.
[10] The cell aggregation control agent according to [9], wherein the peptide that binds to E-cadherin is a peptide composed of the amino acid sequence of SEQ ID NO: 3.
[11] A medium containing the cell aggregation control agent according to any one of [8] to [10].

Effects of the Invention

The present invention enables to provide a method for culturing cells by which the diameter of cell aggregates can be controlled, and by which a large amount of cells can be obtained, a cell aggregate obtained by the method, a cell aggregation control agent, and a medium containing the cell aggregation control agent.

MODE FOR CARRYING OUT THE INVENTION

The culture method of the present invention is a method for culturing cells by suspension culture, and comprises an aggregation control step of adding a substance that inhibits a cell adhesion molecule(s) of the cells to a medium to control cell aggregation of the cells. By the culture method of the present invention, the diameter of the aggregates can be controlled to a uniform diameter, to thereby enable culture of a large amount of cells having uniform quality.

As described below in detail, the method for obtaining the cells to be used for the suspension culture is not limited. The cells are preferably cells having E-cadherin, more preferably stem cells or epithelial cells.

The substance that inhibits a cell adhesion molecule(s) of the cells is preferably at least one selected from cell adhesion molecules, proteins composed of partial regions of cell adhesion molecules, fusion proteins containing the whole or partial regions of cell adhesion molecules, neutralizing antibodies against cell adhesion molecules, peptides that bind to cell adhesion molecules, and derivatives thereof. The cell adhesion molecule is more preferably a molecule belonging to the cadherin family. The molecule belonging to the cadherin family is preferably E-cadherin, or a molecule having structural similarity to this molecule, containing the EC1 domain and one or more of the EC2 domain, EC3 domain, EC4 domain, and EC5 domain related to E-cadherin, and having a homophilic binding capacity to the pluripotent stem cells.

The substance that inhibits a cell adhesion molecule(s) of the cells is more preferably at least one selected from E-cadherin, proteins composed of partial regions of E-cadherin, fusion proteins containing the whole or a partial region of E-cadherin, neutralizing antibodies against E-cadherin, peptides that bind to E-cadherin, and derivatives thereof.

After the aggregation control step, the obtained cell aggregates may be subjected to suspension culture in a medium that does not contain the substance that inhibits a cell adhesion molecule(s). This is because, by uniformly controlling the diameter of the aggregates in the early phase of the aggregation control step, the size of the aggregates can be uniformly controlled even in cases where the subsequent suspension culture is carried out in a medium that does not contain the substance that inhibits a cell adhesion molecule(s). Such subsequent suspension culture in a medium that does not contain the substance that inhibits a cell adhesion molecule(s) is preferred from the viewpoint of increasing the number of cells.

Figure 1:
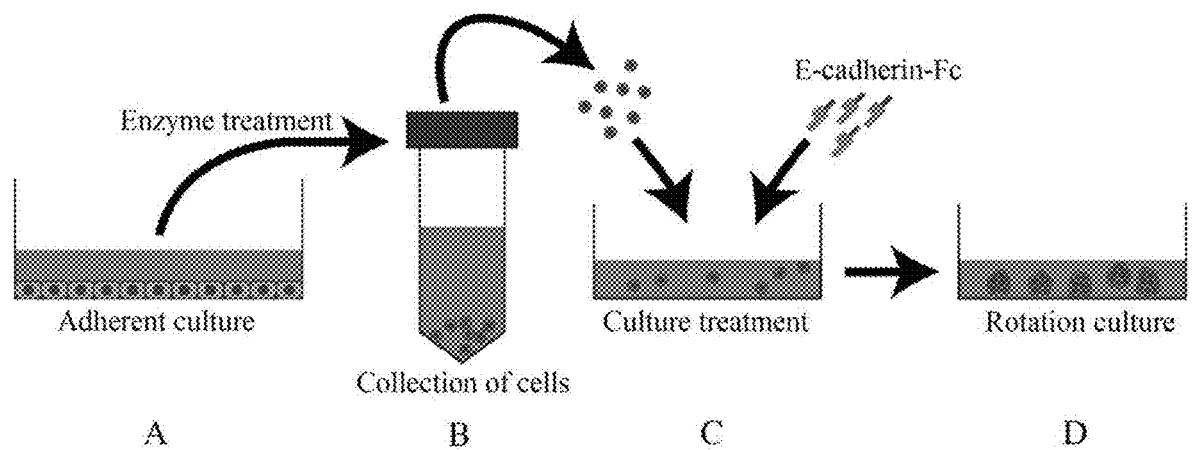
FIG. 1 is an explanatory diagram showing an embodiment of the culture method of the present invention.

As a specific embodiment of the method for culturing cells of the present invention, an example using human iPS cells is described below with reference to FIG. 1, but the present invention is not limited thereto. First, in order to obtain the cells to be subjected to the suspension culture, human iPS cells adhering to Matrigel, which is a common culture substrate, are detached by enzyme treatment (FIG. 1 (A)), and collected (FIG. 1 (B)). In the aggregation control step, the collected iPS cells are mixed with E-cadherin-Fc fusion protein, which is a substance that inhibits a cell adhesion molecule(s) of iPS cells, and suspension culture is then carried out to perform treatment for inhibition of adhesion of the cells to each other (FIG. 1 (C)). E-cadherin is a membrane protein involved in cell-cell adhesion of human iPS cells, and E-cadherin-Fc fusion protein is a recombinant protein in which an antibody Fc tag is attached to the adhesive domain of E-cadherin. By allowing adhesion of E-cadherin-Fc fusion protein to the E-cadherin-adhesive domain on human iPS cells, cell-cell adhesion using E-cadherin is inhibited. Examples of other substances that inhibit E-cadherin include recombinant E-cadherin, E-cadherin antibodies, and E-cadherin-inhibiting peptides. This treatment is carried out for a period of about 1 to 2 days, and rotation culture is carried out using a shaker during this period. After the treatment, the medium is replaced with a normal medium, and medium replacement is carried out every day thereafter (FIG. 1 (D)).

Modes for carrying out the present invention are described below in detail. The term "pluripotent stem cells" as used in the present description means cells having a capacity to grow permanently or for a long period in in vitro culture while maintaining the undifferentiated state, which cells show a normal karyotype (chromosomal type) and have a capacity to differentiate into cells belonging to the lineage of any of the three germ layers (ectoderm, mesoderm, and endoderm) under appropriate conditions. "Pluripotent stem cells" are ES cells, which are isolated from an early embryo, iPS cells, or other similar cells, and examples of the pluripotent stem cells include, but are not limited to, EG cells, which are isolated from primordial germ cells in the fetal period. In the present description. "ES cells" may also include "EG cells".

The term "undifferentiated" as used in the present description means a property that exhibits, in pluripotent stem cells, an undifferentiated state which can be confirmed based on expression of at least one undifferentiation marker, for example, ALP activity, expression of the Oct-3/4 gene(s) (product(s)), and/or expression of various antigen molecules. The undifferentiated state in pluripotent stem cells means a state where the cell growth of the pluripotent stem cells is possible permanently or for a long period, which cells show a normal karyotype (chromosomal type) and have a capacity to differentiate into cells belonging to the lineage of any of the three germ layers under appropriate conditions.

The term "pluripotency of differentiation" as used in the present description means a capacity to differentiate into various types of cells. The differentiated cells are not limited as long as the cells are of a type which can be generally induced by differentiation of pluripotent stem cells. Specific examples of the differentiated cells include ectodermal cells, cells derived from ectodermal cells, mesodermal cells, cells derived from mesodermal cells, endodermal cells, and cells derived from endodermal cells.

The term "medium" as used in the present description includes all liquid media that can be applied to conventional methods for subculture of pluripotent stem cells.

The method for obtaining the cells to be used in the suspension culture in the present invention is not limited, and a culture method which has been conventionally used may be used. The method for culturing the pluripotent stem cells is described below.

As the method for culturing the pluripotent stem cells, any method used for culture of pluripotent stem cells may be used. Examples of such a method include plate culture methods using, for example, a culture dish, or a microplate or plate with 96 wells, 48 wells, or the like; and suspension culture methods using, for example, a flask, bag, reactor, or the like.

In cases where the plate culture is carried out, a cell-adhesive substrate needs to be provided on a surface of a container such as a dish or a plate. Examples of such a cell-adhesive substrate include agar, gelatin, Matrigel, laminin, vitronectin, and E-cadherin. The amount of the cell-adhesive substrate used is not limited as long as it is a concentration used for culture of pluripotent stem cells. The amount is about 2 to 50 µg/ml in terms of the concentration in the aqueous solution for the immobilization on the container.

Examples of methods applicable to immobilization of the adhesive substrate on the solid-phase surface of the container, or to coating of the solid-phase surface of the container with the adhesive substrate, include physical methods such as adsorption and chemical methods such as covalent bonding. From the viewpoint of simplicity of operation, a method by adsorption is preferred. The adsorption can be achieved by bringing a solution containing the adhesive substrate into contact with the surface of the substrate for a predetermined period, preferably for several minutes to one day and night, more preferably for 20 minutes to 12 hours. An antigenic molecule may be artificially attached to/fused with an adhesive molecule in advance, and binding of a specific antibody to the antigenic molecule may be utilized.

The thus prepared culture vessel can be used as it is for a usual culture method for pluripotent stem cells. That is, an appropriate number of pluripotent stem cells may be suspended in a commonly used liquid medium or cell culture medium, and the resulting suspension may be added to the culture substrate. Replacement of the liquid medium and subculture may also be carried out thereafter in the same manner as in conventional methods.

By culturing pluripotent stem cells using the above material, pluripotent stem cells can be obtained in a number required for the suspension culture. Isolation of cells from the cell substrate and collection of the cells are usually carried out by enzyme treatment. Examples of the enzyme used therefor include trypsin, collagenase, hyaluronidase, elastase, and pronase.

[Substance that Inhibits Cell Adhesion Molecule(s)]

The substance that inhibits a cell adhesion molecule(s) used in the culture method of the present invention is a substance capable of inhibiting a cell adhesion molecule(s) involved in aggregability of cells. As described above, the substance is preferably a cell adhesion molecule or a derivative thereof, more preferably at least one selected from E-cadherin, proteins composed of partial regions of E-cadherin, fusion proteins containing the whole or a partial region of E-cadherin, neutralizing antibodies against E-cadherin, peptides that bind to E-cadherin, and derivatives thereof.

Cadherin is an adhesion molecule involved in $Ca^{2+}$-dependent cell-cell adhesion/bonding called adhesive bonding or adherens junction, and known representative examples of cadherin include the E (epithelial) type, N (neural) type, and P (placental) type. These cadherin molecules are membrane-bound glycoprotein molecules composed of 700 to 750 amino acid residues, and the extracellular domain of each molecule has five repeat structures each composed of about 110 amino acid residues, the so-called Extracellular Cadherin (EC) domains. For example, in the case of human E-cadherin (whose amino acid sequence is shown in SEQ ID NO: 1), the EC1, EC2, EC3, EC4, and EC5 domains correspond to 157 to 262, 265 to 375, 378 to 486, 487 to 595, and 596 to 700, respectively (each number represents the residue position in the amino acid sequence of SEQ ID NO: 1). In the case of mouse E-cadherin (whose amino acid sequence is shown in SEQ ID NO: 2), the EC1, EC2, EC3, EC4, and EC5 domains correspond to 159 to 264, 267 to 377, 380 to 488, 489 to 597, and 598 to 702, respectively (each number represents the residue position in the amino acid sequence of SEQ ID NO: 2). These EC domains have homologies among different cadherin molecular species, and domains positioned in the N-terminal side (EC1 and EC2) have especially high homologies. As cadherin molecules having such similar structures, not less than 50 types of molecules are known at present, and these molecules are collectively called the cadherin family. For reviews on cadherin, see, for example, Takeichi, Curr. Opin. Cell Biol. 7: 619, 1995: Marrs & Nelson, Int. Rev. Cytol. 165: 159, 1996; Yap et al., Annu. Rev. Cell Dev. Biol. 13: 119, 1997; Yagi & Takeichi, Genes Dev. 14: 1169, 2000; and Gumbiner, J. Cell Biol. 148: 399, 2000.

Expression of E-cadherin (another name, cadherin-1) is widely found in parenchymal cells of internal organs such as liver, kidney, and lung, and epithelial cells such as keratinocytes, and E-cadherin is known to be an important adhesion molecule responsible for their cell-cell adhesion (for reviews, see, for example. Mareel et al., Int. J. Dev. Biol. 37: 227, 1993; Mays et al., Cord Spring Harb. Symp. Quant. Biol. 60: 763, 1995; El-Bahrawy & Pignatelli, Microsc. Res. Tech. 43: 224, 1998; Nollet et al., Mol. Cell. Biol. Res. Commun. 2: 77, 1999).

The method for preparing a protein belonging to E-cadherin is not limited. It is preferred to use a recombinant protein prepared and purified using molecular biological methods. Besides this, any method may be used as long as it is a method which exhibits a similar effect. For example, a protein belonging to E-cadherin of pluripotent stem cells may be extracted and purified from a biological tissue/cells, or the peptide may be chemically synthesized.

For example, the E-cadherin gene has been isolated and identified from animals such as human (SEQ ID NO: 1), mouse (SEQ ID NO: 2), and rat, and their base sequences are available in public DNA databases by NCBI and the like (accession numbers: (human) NM_004360; (mouse) NM_009864; (rat) NM_031334). Thus, those skilled in the art can obtain and use cDNA of the E-cadherin gene by designing a primer(s) and/or a probe(s) specific to the E-cadherin gene, and using common molecular biological methods. cDNA of the E-cadherin gene can also be purchased from RIKEN Gene Bank (Tsukuba, Japan), American Type Culture Collection (ATCC), Invitrogen/ResGen, and the like. The gene encoding the protein belonging to the cadherin family used is preferably one derived from the same animal species as the species from which the pluripotent stem cells are derived. For example, in cases where mouse ES cells are used to carry out the present invention, mouse E-cadherin cDNA is preferably used. However, E-cadherin cDNA derived from a different animal species, that is, E-cadherin cDNA derived from human, monkey, cow, horse, pig, sheep, or a bird (for example, chicken), or an amphibian (for example, *Xenopus laevis*) may also be used.

A preferred example of the method for preparation of the recombinant protein of a protein belonging to E-cadherin is characterized in that a gene encoding the molecule is introduced into mammalian cells such as COS cells, 293 cells, or CHO cells, and allowing expression of the gene. The gene is preferably linked to a nucleic acid sequence that enables transcription and expression of the gene in a wide variety of mammalian cells, that is, the so-called promoter sequence, such that the transcription and expression are possible under the control of the promoter. The gene to be transcribed and expressed is preferably further linked to a poly(A) addition signal. Preferred examples of the promoter include promoters derived from viruses such as SV (Simian Virus) 40 virus, Cytomegaro Virus (CMV), and Rous sarcoma virus; β-actin promoter; and EF (Elongation Factor) 1α promoter.

The gene used for the preparation of the recombinant protein does not necessarily need to contain the entire region of a gene encoding the molecule, and may be a partial gene sequence as long as the level of adhesion activity of the protein or peptide molecule encoded by the partial sequence is almost the same as, or higher than, that of the original molecule. For example, in cases of E-cadherin, which is used for preferred cases in the present invention, a recombinant protein prepared from a partial sequence encoding the extracellular domain containing 690 to 710 amino acid residues from the N-terminus, that is, a protein containing the EC1 to EC5 domains, may be used. In general, in cadherin molecules, the domain positioned closest to the N-terminus (EC1) defines the binding specificity, that is, homophilicity, of the molecule (Nose et al., Cell 61: 147, 1990). Therefore, a protein molecule which contains at least EC1, but does not contain one or several other domains may be prepared and used. Further, a protein which exhibits an amino acid homology of not less than 80%, preferably not less than 85%, more preferably not less than 90%, most preferably not less than 95% to the protein molecule described above, and which has the adhesion activity, may also be used.

The recombinant protein may also be prepared as a fusion protein with another protein or peptide. For example, the recombinant protein may be prepared as a fusion protein with the Fc region of an immunoglobulin, with GST (Glutathione-S-Transferase) protein, with MBP (Mannnose-Binding Protein) protein, with avidin protein, with a His (oligohistidine) tag, with an HA (HemAgglutinin) tag, with a Myc tag, with a VSV-G (Vesicular Stromatitis Virus Glycoprotein) tag, or the like, and the prepared fusion protein may be applied to a protein A/G column, specific antibody column, or the like to allow easy and efficient purification of the recombinant protein. Fc fusion proteins are especially preferred for carrying out the present invention since they form dimers and hence have stable activity as proteins.

Genes encoding the Fc regions of immunoglobulins have already been isolated and identified in mammals including human. A large number of their base sequences have also been reported. For example, sequence information on base sequences containing the Fc regions of human IgG1, IgG2, IgG3, and IgG4 is available in public DNA databases in NCBI and the like, wherein those sequences are deposited under accession numbers: AJ294730, AJ294731, AJ294732, and AJ294733, respectively. Thus, those skilled in the art can obtain and use cDNA encoding an Fc region portion by designing a primer(s) and/or a probe(s) specific to the Fc region, and using common molecular biological methods. In such cases, the animal species and the subtype of the gene encoding the Fc region used are not limited. Genes encoding Fc regions having a strong binding capacity to protein A/G, such as human IgG1 and IgG2, and mouse IgG2a and IgG2b, are preferred. A method in which the binding capacity to protein A is enhanced by introduction of a mutation(s) to the Fc region is also known (see Nagaoka et al., Protein Eng. 16:

243, 2003). An Fc protein prepared by gene modification by this method may also be used.

In cases of E-cadherin, which is preferably used for carrying out the present invention, an example of the production method for the recombinant protein has been reported (see Nagaoka et al., Biotechnol. Lett. 24: 1857, 2002; Protein Eng. 16: 243, 2003).

A purified recombinant protein prepared by introducing a fusion gene prepared by linking cDNA of a sequence encoding the Fc region portion of human IgG and a His tag sequence to cDNA encoding the extracellular domain of mouse or human E-cadherin into mouse cells and allowing expression of the fusion gene (Recombinant Human/Mouse E-cadherin-Fc Chimera; R&D systems; Genzyme Techne) is commercially available, and this protein may also be used as a mouse- or human-derived E-cadherin protein (E-Cad-Fc protein).

The method for preparing the peptide that binds to a cell adhesion molecule(s) such as E-cadherin is not limited. For example, using a cell adhesion molecule such as E-cadherin as a target molecule, affinity selection which is conventionally carried out such as phage display may be used to perform screening (for example, Devemy E, Blaschuk O. Identification of a novel N-cadherin antagonist. Peptides 2008; 29: 1853-61). One specific example of the method is as follows. First, peptides selected from a peptide library are placed in wells of a plate that are preliminarily coated with E-cadherin-Fc fusion protein, and the plate is then incubated. Subsequently, the wells are washed for removal of unbound phages. Bound phages are eluted in two steps. The first elution step is carried out using TBS supplemented with 2 mM EDTA, and elution in the second elution step is carried out using 0.2 M glycine-HCl (pH 2.2). The eluate at pH 2.2 is neutralized using 1 M Tris-HCl (pH 9.1). By infection of ER2738 cells with each eluted phage fraction, the phages are amplified. The amplified phages are purified by polyethylene glycol precipitation. The phages amplified from the EDTA fraction were used for the second biopanning operation, and only the EDTA eluate was used for the third biopanning operation. The phages amplified from the acid fraction were used for the second biopanning operation, and only the acid eluate was amplified and used for the final biopanning operation. At the end of the screening, the phages are plated, and isolated clones are randomly collected and amplified. Single-stranded DNA is extracted from each phage clone, and its amino acid sequence is deduced by DNA sequencing. Examples of peptides that bind to E-cadherin include SWELYYPLRANL, which is shown in the amino acid sequence of SEQ ID NO: 3, and the peptides shown in the amino acid sequences of SEQ ID Nos: 4 to 30. These peptides may have a conventionally known modification(s) (for example, PEGylation and/or C-terminal amidation) as long as binding to the target molecule is not lost. These peptides may be used individually, or two or more of these may be used in combination.

The method for preparing the neutralizing antibody against a cell adhesion molecule such as E-cadherin is not limited, and known methods which have been conventionally carried out may be employed. A peptide that binds to the cell adhesion molecule such as E-cadherin may be prepared as an antibody and used. Examples of such a method include a method in which an antibody is prepared by immunizing an animal using as an antigen a cell adhesion molecule or a peptide that binds to a cell adhesion molecule, and a method in which the gene of the protein of interest incorporated in an expression vector is introduced to an animal, and the gene is expressed in the body of the animal, to prepare an antibody using the protein of interest as an antigen, followed by collecting the antibody (DNA immunization method).

In the present description, the protein composed of a partial region of a cell adhesion molecule or E-cadherin means a protein in which one or more molecules are absent compared to the parent molecule of the cell adhesion molecule or E-cadherin, which protein has cell adhesiveness.

In the present description, the derivative means a molecule showing one or more differences in its sequence compared to the parent molecule, which molecule has cell adhesiveness. Examples of the derivative include reaction products between the whole or a part of a cell adhesion molecule or E-cadherin, and another chemical substance or a low-molecular-weight polymer component or oligomer component. The homology of the derivative to the parent molecule is preferably not less than 75%, more preferably not less than 85%, still more preferably not less than 90%.

[Aggregation Control Step]

The aggregation control step in the culture method of the present invention is a step of adding a substance that inhibits a cell adhesion molecule(s) of the cells to be cultured to a medium to control cell aggregation of the cells. In the aggregation control step, a desired medium may be placed in a container, and the cells and the substance that inhibits a cell adhesion molecule(s) may be included in the medium, followed by performing suspension culture while leaving the mixture to stand or carrying out stirring or the like. By this, the substance that inhibits a cell adhesion molecule(s) can be allowed to act on the cell surface, to thereby control cell-cell adhesiveness such that aggregates having a desired size can be obtained.

The amount of the substance that inhibits a cell adhesion molecule(s) added in this step is appropriately selected depending on the amount of the cells and components in the medium. In particular, the amount of the substance is appropriately selected such that the size (diameter) of the aggregates 48 hours after the beginning of the suspension culture by addition of the substance that inhibits a cell adhesion molecule(s) is not less than 20 μm and less than 1 mm. For example, in cases where a protein belonging to E-cadherin or a neutralizing antibody is used, it is preferably added to a concentration of 5 to 100 μg/ml, and, in cases where a peptide that binds to a cell adhesion molecule(s) such as E-cadherin is used, it is preferably added to a concentration of 0.01 to 1000 μM. In cases where the amount of the substance added is smaller than the range described above, the size of the aggregates obtained may be too large, so that survival of the cells in the inner side of the aggregates may be impossible, or, when stem cells are used, the cells may lose undifferentiation. In cases where the amount exceeds the range described above, aggregates having remarkably uneven sizes may be obtained, or the surfaces of large aggregates may be covered with small aggregates, so that survival of the cells in the large aggregates may be impossible. From the viewpoint of obtaining a large amount of homogeneous cells, when a protein belonging to E-cadherin or a neutralizing antibody is used, its concentration is preferably 7 to 80 μg/ml, more preferably within the range of 8 to 65 μg/ml, still more preferably within the range of 10 to 50 μg/ml. When a peptide that binds to a cell adhesion molecule(s) such as E-cadherin is used, its concentration is preferably 0.1 to 900 μM, more preferably within the range of 0.5 to 800 μM, still more preferably within the range of 1 to 600 μM. In cases where the concentration is within the above-described ranges, the size of the aggregates after 48 hours can be controlled to not less than 20 μm and less than 1 mm. By controlling the size of the aggregates to this size, the size of the aggregates finally obtained can be made uniform, and, as a result, the cell survival rate and the number of cells can be increased. This is thought to be because, unlike conventional methods which simply make cells less adhesive to each other, the substance that inhibits a cell adhesion molecule(s) in the present invention directly acts on an adhesion factor(s) to enable cellular-level control of the level of adhesion between cells.

When a protein belonging to E-cadherin or a neutralizing antibody is used, the amount of the substance that inhibits a cell adhesion molecule(s) is, taking into account the protein adsorption property depending on the protein content in the medium, within the range of 25 to 100 µg/ml, 30 to 100 µg/ml, preferably 40 to 100 µg/ml, more preferably 50 to 100 µg/ml in cases where a medium with a low protein content (for example, with a protein content of not more than 1 mg/ml) is used, or within the range of 7 to 80 µg/ml, preferably 8 to 65 µg/ml, more preferably 10 to 50 µg/ml in cases where a medium with a high protein content (for example, with a protein content of not less than 10 mg/ml) is used. By adding the substance that inhibits a cell adhesion molecule(s) in such an amount, secure blocking of cell membrane cadherin is possible since the substance that inhibits a cell adhesion molecule(s) is adsorbed to another cell membrane or culture substrate before blocking of the cell membrane cadherin of interest.

The length of time of the treatment of the cells after addition of the substance that inhibits a cell adhesion molecule(s) may be appropriately determined depending on the size of the aggregates. The length of time is usually 24 to 48 hours. In cases where the treatment time is less than this length, formation of the aggregates may be difficult in some cases, while in cases where the length of time is longer than this range, the aggregates hardly grow, leading to a small number of cells obtained.

As described above, in the culture method of the present invention, from the viewpoint of increasing the number of cells, the cell aggregates obtained in the aggregation control step are preferably subjected to normal suspension culture, that is, suspension culture in a medium that does not contain the substance that inhibits a cell adhesion molecule(s). In this process, the culture may be stopped when the sizes of all aggregates are not less than 250 µm and less than 1 mm, preferably within the range of about 250 to 950 µm, more preferably within the range of about 300 to 750 µm, still more preferably within the range of about 300 to 600 µm.

In the present invention, the method of suspension culture is not limited as long as it is a method in which cells are subjected to suspension culture in a container such as a bag, flask, or reactor. The suspension culture may be static culture, but, from the viewpoint of giving nutrients and oxygen to the cells, the culture is preferably carried out under conditions where these can be given, for example, under conditions accompanied by stirring, flow, or the like.

Preferred examples of conditions for the stirring include stirring at about 20 to 150 rpm. Examples of methods, other than stirring, for giving nutrients and oxygen include the bubbling method, in which a gas is included in the culture liquid, and a method in which the culture liquid is circulated. Examples of methods for giving oxygen other than the methods described above include a method in which hemoglobin is included in the culture liquid to enable efficient supply of oxygen.

The medium used in the suspension culture of the present invention is not limited, and a medium which is used for cell culture and suitable for the type of the cells may be used. The medium for culture of pluripotent stem cells is described below in detail. The liquid medium for culture of pluripotent stem cells is not limited as long as it is applicable to a conventional method for subculturing pluripotent stem cells. Specific examples of the liquid medium include Dulbecco's Modified Eagle's Medium (DMEM), Glasgow Minimum Essential Medium (GMEM), and RPM11640 medium. These media are usually used after addition of about 2 mM glutamine and/or about 100 µM 2-mercaptoethanol. KnockOut® DMEM (Invitrogen), ES cell-qualified DMEM (Cell & Molecular Technologies), TX-WES (Thromb-X), and the like which are commercially available as media for culturing ES cells may also be used. These media are preferably supplemented with 5 to 25% FBS, but serum-free culture may also be carried out by using, for example, 15 to 20% KnockOut® Serum Replacement (Invitrogen) instead. A culture supernatant of MEF cells, or a medium supplemented with bFGF/FGF-2, SCF, and/or the like may also be used. Details of such a method are known (Xu et al., Nature Biotech. 19: 971, 2001; WO 01/51616; WO 03/020920; Amit et al., Biol. Reprod., 70: 837, 2004). Examples of the liquid medium used for culture of pluripotent stem cells include, besides those described above, conventionally used known media such as Dulbecco's Modified Eagles's Medium (DMEM). DMEM/F12 medium, McCoy's 5A medium, Ham's Nutrient Mixture F12. MEM medium (Minimum Essential Medium), αMEM medium (alpha Modified Eagles's Minimum Essential Medium; αMEM) Eagles's MEM medium (Eagles's Minimum Essential Medium; EMEM), RPMI 1640 medium, IPL 41 medium, Iscove's Modified Dulbecco's Medium (IMDM), William's medium E, MCDB 131 medium, Fischer's medium, StemPro® 34 (manufactured by Invitrogen), StemPro® hESC SFM (manufactured by Invitrogen), Sf-900® II (manufactured by Invitrogen), Opti-Pro (manufactured by Invitrogen), X-VIVO® 10 (manufactured by Cambrex Corporation), X-VIVO® 15 (manufactured by Cambrex Corporation), HPGM® (manufactured by Cambrex Corporation), StemSpan® H3000 (manufactured by StemCell Technologies Inc.), StemSpan® SFEM (manufactured by StemCell Technologies Inc.), mTeSR®1 or 2 medium (manufactured by StemCell Technologies Inc.), Stemline® II (manufactured by Sigma Aldrich), QBSF®-60 (manufactured by Quality Biological, Inc.), Essential 8® medium (manufactured by Gibco), MesenPRO RS® medium (manufactured by Gibco), Repro FF or Repro FF2 (manufactured by ReproCELL Inc.), PSGro hESC/iPSC medium (manufactured by System Biosciences, Inc.), NutriStem® medium (manufactured by Biological Industries), CSTI-7 medium (manufactured by Cell Science & Technology Institute, Inc.), and MF-Medium mesenchymal stem cell growth medium (manufactured by Toyobo Co., Ltd.).

In cases where a medium containing a large amount of protein such as albumin (for example, a medium whose protein content is not less than 10 mg/ml) is used, adsorption of protein to cell membrane surfaces, the culture substrate, and the like tends to be suppressed due to the protein in the medium. In cases where a medium containing a small amount of protein (for example, a medium whose protein content is not more than 1 mg/ml) is used, adsorption of protein to cell membrane surfaces, the culture substrate, and the like is more likely to occur compared to cases where a medium containing a large amount of protein is used.

Further, the medium may also contain a component conventionally used for culture of pluripotent stem cells, such as sodium, potassium, calcium, magnesium, phosphorus, chlorine, amino acid, vitamin, antibiotic, serum, fatty acid, or sugar, depending on the purpose. In culture of cells and/or a tissue derived from an animal, the medium may also contain one or more kinds of other chemical components and biological components in combination depending on the purpose.

Examples of the component(s) added to the medium for cells and/or a tissue derived from an animal include fetal bovine serum, human serum, horse serum, insulin, transferrin, lactoferrin, cholesterol, ethanolamine, bovine serum albumin, sodium selenite, monothioglycerol, 2-mercaptoethanol, polyethylene glycol, sodium pyruvate, vitamins, amino acids, agar, agarose, collagen, methylcellulose, cytokines, hormones, growth factors, extracellular matrices, and cell adhesion molecules.

Examples of the cytokines include interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-1 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (TFN-α), interferon-β (IFN-β), interferon-γ (IFN-γ), granulocyte colony-stimulating factor (G-CSF), monocyte colony-stimulating factor (M-CSF), granulocyte-macrophage colony-stimulating factor (GM-CSF), stem cell factor (SCF), leukemia cell inhibitory factor (LIF), flk2/flt3 ligands (FL), oncostatin M (OM), erythropoietin (EPO), and thrombopoietin (TPO).

Examples of the hormones include melatonin, serotonin, thyroxine, triiodothyronine, epinephrine, norepinephrine, dopamine, adiponectin, anti-Mullerian hormone, adrenocorticotropic hormone, angiotensinogen, angiotensin, antidiuretic hormone, atrial natriuretic peptide, calcitonin, cholecystokinin, corticotropin releasing hormone, erythropoietin, follicle-stimulating hormone, gastrin, ghrelin, glucagon, gonadotropin releasing hormone, growth hormone releasing hormone, human chorionic gonadotropin, human placental lactogen, growth hormone, insulin, insulin-like growth factor, inhibin, leptin, luteinizing hormone, melanocyte-stimulating hormone, parathyroid hormone, thyroid stimulating hormone, thyrotropin releasing hormone, oxytocin, secretin, somatostatin, thrombopoietin, prolactin, cortisol, aldosterone, testosterone, dehydroepiandrosterone, androstenedione, dihydrotestosterone, estradiol, estrone, estriol, progesterone, calcitriol, calcidiol, prostaglandin, prostacyclin, leukotrien, thromboxane, prolactin-releasing hormone, lipotropin, brain natriuretic peptide, neuropeptide Y, histamine, endothelin, pancreatic polypeptide, renin, and enkephalin.

Examples of the growth factors include, but are not limited to, transforming growth factor-α (TGF-α), transforming growth factor-β (TGF-β), macrophage inflammatory protein-1α (MTP-1α), epidermal growth factor (EGF), fibroblast growth factor-1, 2, 3, 4, 5, 6, 7, 8, and 9 (FGF-1, 2, 3, 4, 5, 6, 7, 8, and 9), nerve cell growth factor (NGF), leukemia inhibitory factor (LIF), hepatocyte growth factor (HGF), platelet-derived growth factor (PDGF), protease nexin I, protease nexin II, cholinergic differentiation factor (CDF), chemokine, Notch ligands (Delta1 and the like), Wnt protein, angiopoietin-like proteins 2, 3, 5, and 7 (Angpt 2, 3, 5, and 7), insulin-like growth factor (IGF), insulin-like growth factor binding protein (IGFBP), and Pleiotrophin.

The medium may also contain a product produced by artificially modifying an amino acid sequence of a cytokine or a growth factor described above by genetic recombination. Examples of such a product include IL-6/soluble IL-6 receptor complex and Hyper IL-6 (fusion protein of IL-6 and soluble IL-6 receptor).

Examples of the extracellular matrices and cell adhesion molecules include collagen I to XIX, fibronectin, vitronectin, laminin-1 to 12, nitogen, tenascin, thrombospondin, von Willebrand factor, osteopontin, fibrinogen, elastins, proteoglycans, cadherins, integrins, desmocollin, desmoglein, E-selectin, P-selectin, L-selectin, immunoglobulin superfamily, poly-D-lysine, poly-L-lysine, chitin, chitosan, sepharose, hyaluronic acid. Matrigel, alginate gel, and hydrogels, as well as cleaved fragments thereof.

Examples of the antibiotics include sulfa preparations, penicillin, ampicillin, phenethicillin, methicillin, nafcillin, oxacillin, cloxacillin, dicloxacillin, flucloxacillin, amoxicillin, cyclacillin, carbenicillin, ticarcillin, piperacillin, azlocillin, meczlocillin, amdinocillin, mecillinam, cephalosporin and derivatives thereof, oxolinic acid, amifloxacin, temafloxacin, nalidixic acid, piromidic acid, pipemidic acid, clavulanic acid, β-bromopenicillanic acid, β-chloropenicillanic acid, 6-acetylmethylene-penicillanic acid, ciprofloxacin, cinoxacin, norfloxacin, perfloxacin, rosaxacin, ofloxacin, enoxacin, sulbactam, cefoxazole, sultampicillin, formaldehyde-hydrate ester of adinocillin and sulbactam, tazobactam, aztreonam, sulfazethin, isosulfazethin, norcardicin, m-carboxyphenyl, phenylacetamide methyl phosphonate, chlortetracycline, oxytetracycline, tetracycline, demeclocycline, doxycycline, methacycline, and minocycline.

The aggregate of the present invention is a cell aggregate obtained by the culture method of the present invention, and has a uniform aggregation diameter. A large number of cells can be obtained from the aggregate of the present invention, and all of the obtained cells maintain undifferentiation and pluripotency of differentiation. From the viewpoint of the growth ability and pluripotency of differentiation, the diameters of all aggregates after 48 hours in the suspension culture are not less than 20 μm and less than 1 mm, preferably within the range of 20 to 950 μm, more preferably within the range of 20 to 750 μm, still more preferably within the range of 50 to 500 Fun, especially preferably within the range of 100 to 300 μm.

The cell aggregation control agent of the present invention comprises a substance that inhibits a cell adhesion molecule(s). The cell aggregation control agent of the present invention is preferably used for control of the particle size of aggregates in suspension culture of cells. The substance that inhibits a cell adhesion molecule(s) is not limited, and preferably at least one selected from E-cadherin, proteins composed of partial regions of E-cadherin, fusion proteins containing the whole or a partial region of E-cadherin, neutralizing antibodies against E-cadherin, peptides that bind to E-cadherin, and derivatives thereof.

The culture method of the present invention is very useful as a method for culturing stem cells, which method enables production of a large amount of cells, especially pluripotent stem cells such as iPS cells and ES cells, having uniform quality. The culture, cell aggregate, cell aggregation control agent, and medium of the present invention are very useful in the fields of regenerative medicine and drug discovery.

EXAMPLES

The present invention is described below in more detail by way of Examples. However, the present invention is not limited by these Examples.

<Providing of Pluripotent Stem Cells>

An aqueous Matrigel solution (50-fold dilution in DMEM) was placed in an untreated tissue culture 6-well plate (manufactured by Iwaki & Co., Ltd.) at 1 mL/well, and incubated at 37° C. for 2 hours. Thereafter, the coating agent was removed to provide a human iPS cell culture plate.

As pluripotent stem cells, hiPS cells (TkDN4-M, Stem Cell Bank, The University of Tokyo) were used. These cells were plated on the above culture plate at a density of 100,000 to 400,000 cells/well, and cultured for four days. The culture was carried out using, as a culture medium, 2 mL/well of mTeSR®1 (manufactured by StemCell Technologies). During the culture, medium replacement was carried out every day except for the day after the plating.

For detachment and collection of cells, TrypLE® select (manufactured by Life Technologies), which is a trypsin-like enzyme, was used. After removal of the culture liquid, TrypLE® select was added to the wells at 1 mL/well, and the plate was incubated at 37° C. for 2 to 5 minutes. Thereafter, TrypLE® select was removed, and mTeSR®1 supplemented with 10 µM Y-27632, which is a ROCK inhibitor, was added to the wells at 2 mL/well, followed by pipetting using a 1000-µL micropipette to detach the cells. The collected cell suspension was passed through a 40-µm cell strainer (BD) to collect the cells as single cells and/or microaggregates, to thereby obtain cells to be applied to suspension culture.

<Expression and Purification of E-Cadherin-Fc Fusion Protein>

Expression and purification of E-cadherin-Fc fusion protein were carried out according to Nagaoka M, Akaike T., ProteinEng. 2003; 16: 243-245. In the present Example, extracellular domain cDNA obtained from mouse full-length E-cadherin (RIKEN BRC DNA Bank, code 1184) and mutated IgG1-Fc domain cDNA (T252M/T254S) were ligated, and E-cad-Fc fusion protein was expressed.

<Measurement of Diameters of Cell Aggregates>

In the following Examples and Comparative Examples, morphology and sizes of cell aggregates during the culture period were observed and measured using a phase-contrast microscope (product name, DM IRB; manufactured by LEICA).

Example 1

Example 1-1

To a 12-well plate subjected to low-cell-adhesion treatment, 1 mL/ml of mTeSR®1 was added, and hiPS cells ($2\times10^5$ cells/ml) provided in advance and, as a substance that inhibits a cell adhesion molecule(s) of the hiPS cells, E-cadherin-Fc (5 µg/ml) were added at the same time, followed by performing rotation culture at a speed of 90 to 120 rpm for 48 hours. The sizes of the aggregates 48 hours after the E-cadherin-Fc treatment were within the range of 300 to 700 µm. Subsequently, medium replacement was carried out, and culture was carried out for three days under the same conditions as described above except that E-cadherin-Fc was not added, to obtain aggregates. The sizes of the aggregates were within the range of 500 to 1000 µm.

Example 1-2

Aggregates were obtained in the same manner as in Example 1-1 except that the concentration of E-cadherin-Fc in Example 1-2 was 10 µg/ml. The sizes of the aggregates 48 hours after the E-cadherin-Fc treatment were within the range of 200 to 400 µm. The sizes of the aggregates obtained by the medium replacement and the three days of culture without addition of E-cadherin-Fc were within the range of 300 to 1000 µm.

Example 1-3

Aggregates were obtained in the same manner as in Example 1-1 except that the concentration of E-cadherin-Fc in Example 1-3 was 20 µg/ml. The sizes of the aggregates 48 hours after the E-cadherin-Fc treatment were within the range of 100 to 500 µm. The sizes of the aggregates obtained by the medium replacement and the three days of culture without addition of E-cadherin-Fc were within the range of 300 to 600 µm.

Example 1-4

Aggregates were obtained in the same manner as in Example 1-1 except that the concentration of E-cadherin-Fc in Example 1-4 was 50 µg/ml. The sizes of the aggregates 48 hours after the E-cadherin-Fc treatment were within the range of 100 to 300 µm. The sizes of the aggregates obtained by the medium replacement and the three days of culture without addition of E-cadherin-Fc were within the range of 300 to 600 µm.

Example 1-5

Aggregates were obtained in the same manner as in Example 1-1 except that the concentration of E-cadherin-Fc in Example 1-5 was 100 µg/ml. The sizes of the aggregates 48 hours after the E-cadherin-Fc treatment were within the range of 150 to 700 µm. The sizes of the aggregates obtained by the medium replacement and the three days of culture without addition of E-cadherin-Fc were within the range of 300 to 1000 µm.

Comparative Example 1-1

Aggregates were obtained in the same manner as in Example 1-1 except that E-cadherin-Fc was not used in Comparative Example 1-1. The sizes of the aggregates 48 hours after the E-cadherin-Fc treatment were within the range of 1000 to 3000 µm. The sizes of the aggregates obtained by the three days of culture were also within the range of 1000 to 3000 µm.

<Observation of Cell Aggregates>

Figure 2:
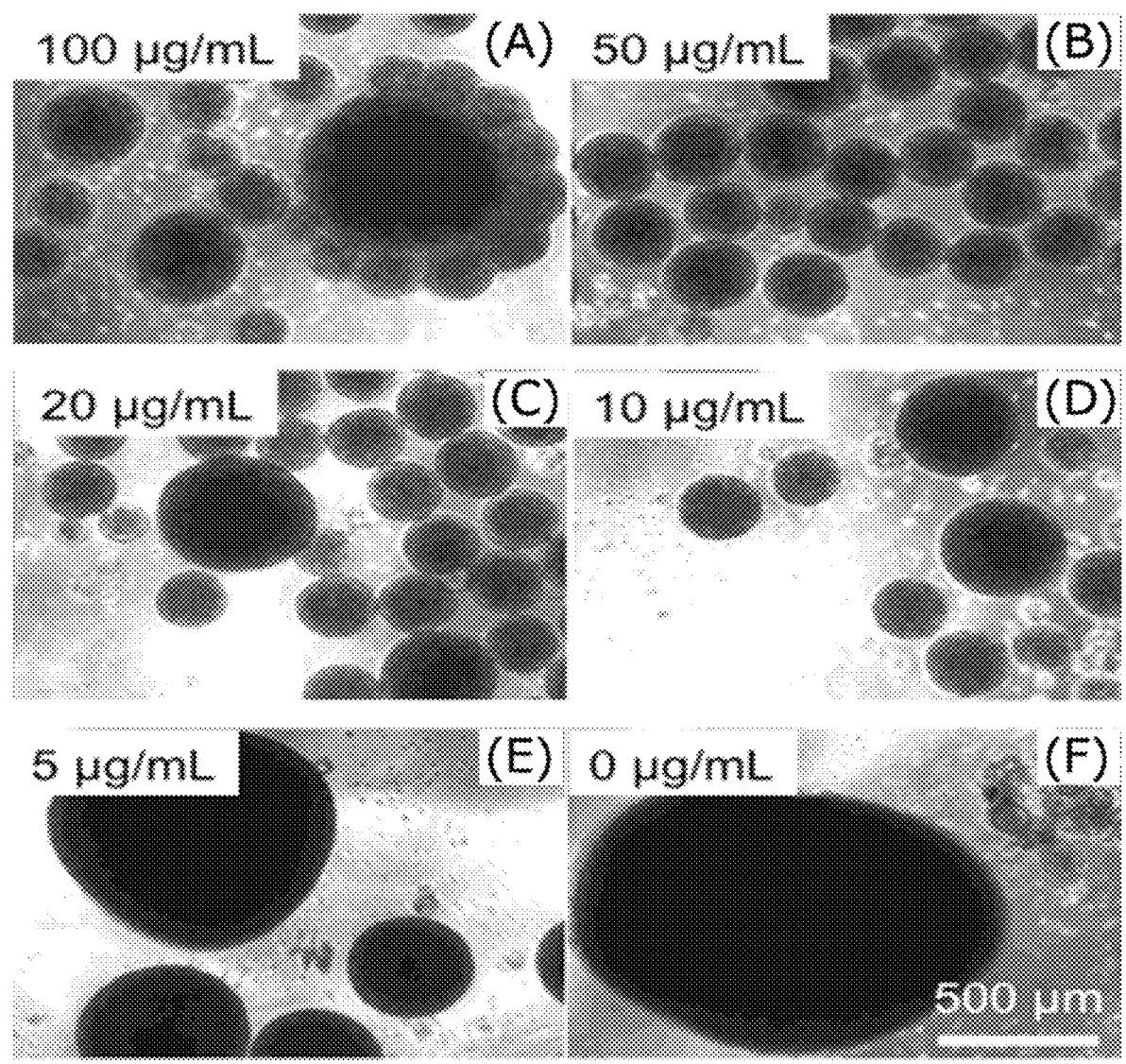
FIG. 2 shows photograph diagrams ((A) to (F)) showing the shapes of aggregates obtained in Examples 1-1 to 1-5 and Comparative Example 1-1, wherein human iPS cells were treated with E-cadherin-Fc in an amount of 0, 5, 10, 20, 50, or 100 μg/ml and then subjected to rotation suspension culture for 5 days, which photographs were taken with a phase-contrast microscope. The scale bar represents 500 μm.

In Examples 1-1 to 1-5 and Comparative Example 1-1, morphology of cell aggregates on Day 2 of the culture (after 48 hours of treatment with E-cadherin-Fc) was observed using a phase-contrast microscope (product name, DM IRB; manufactured by LEICA). The obtained micrographs are shown in FIG. 2 (A) to (F). From FIG. 2 (A) to (F), it can be seen that the aggregates obtained in Examples 1-1 to 1-5 (E-cadherin-Fc concentrations=5, 10, 20, 50, and 100 µg/ml, respectively) have better-controlled sizes as compared to the aggregates obtained in Comparative Example 1-1 (E-cadherin-Fc concentration=0 pig/ml). It can be seen, in particular, that use of E-cadherin-Fc at a concentration within the range of 10 to 50 µg/ml was effective for suppression of excessive aggregation and achievement of formation of uniform aggregates even by simple rotation culture.

<Measurement of Glucose Consumption>

During the whole culture period, 300 µL of the culture liquid was collected upon replacement of the medium, and the glucose concentration was analyzed using an enzyme-electrode type bioanalyzer (YS12950) to calculate changes in the glucose consumption. The results are shown in FIG. 3.

<Measurement of Cell Number>

After completion of the culture, the cells were dispersed into single cells using TrypLE® select, and the number of live cells was counted using trypan blue (manufactured by Life Technologies) and an eosinophil counter (manufactured by Tatai). The results are shown in FIG. 4.

Figure 3:
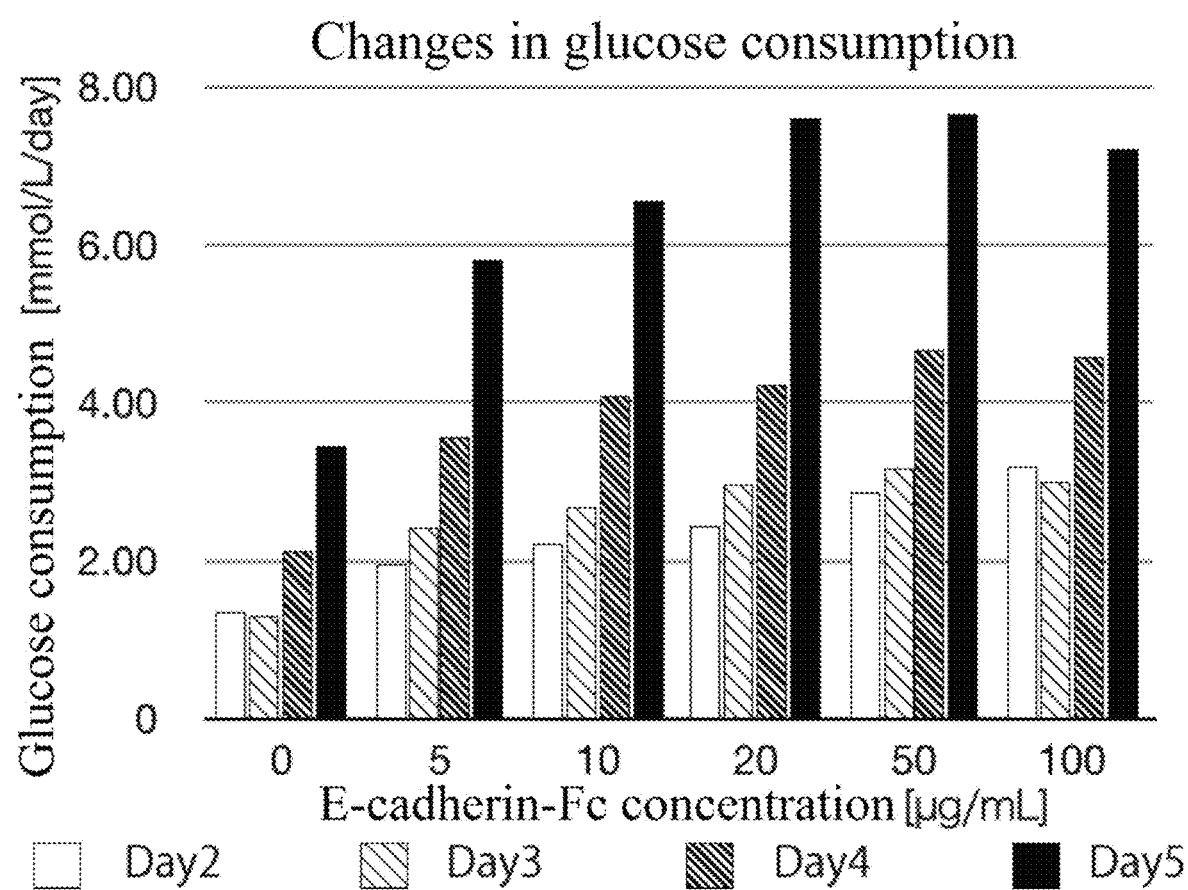
FIG. 3 is a graph diagram showing the glucose consumption of cells as measured for the culture media used in Examples 1-1 to 1-5 and Comparative Example 1-1.
Figure 4:
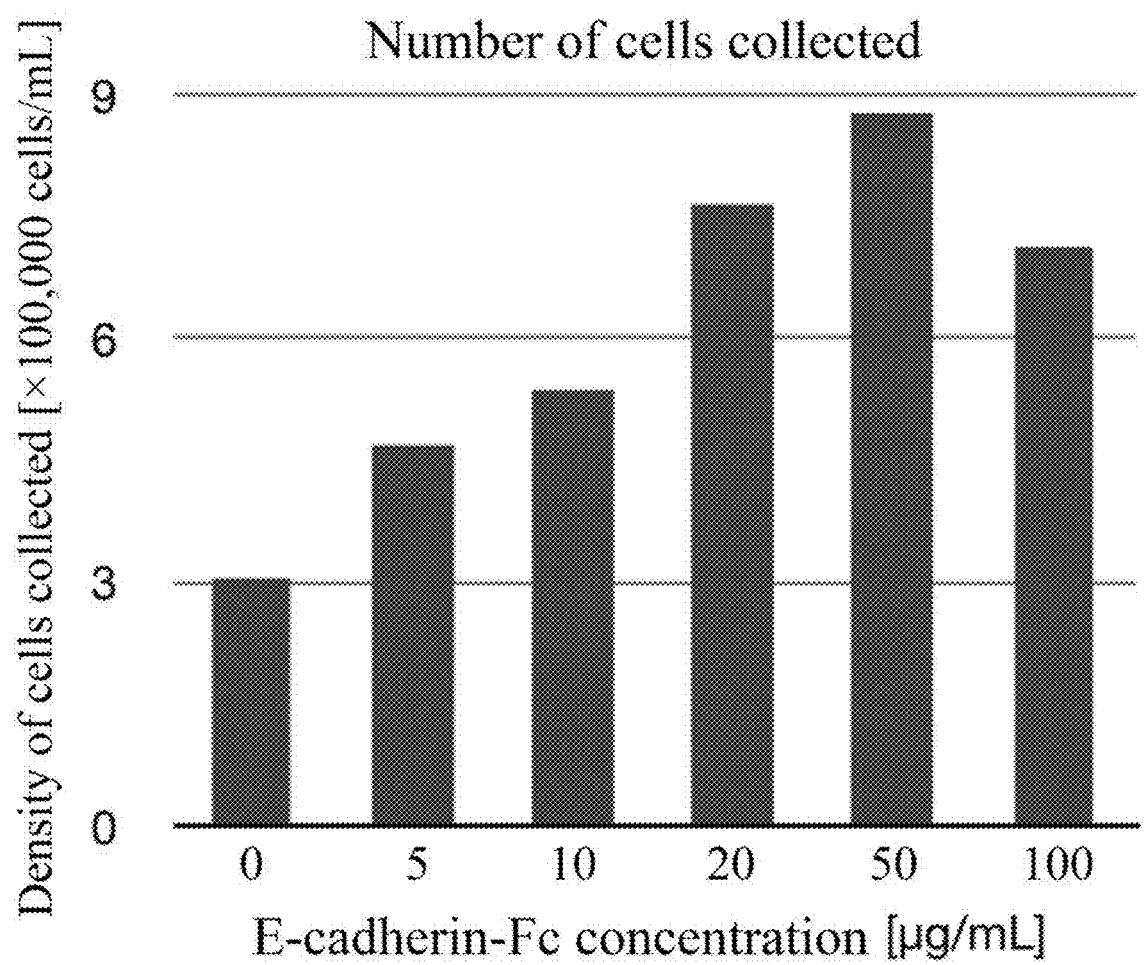
FIG. 4 is a graph diagram showing the densities of cells per 1 ml of medium, which cells were collected after 5 days of culture in Examples 1-1 to 1-5 and Comparative Example 1-1.

Based on the graphs shown in FIGS. 3 and 4, the glucose consumption can be used as an index of the number of living cells. From the results shown in FIGS. 3 and 4, it can be seen that the aggregates obtained in Examples 1-1 to 1-5 (E-cadherin-Fc concentrations=5, 10, 20, 50, and 100 µg/ml, respectively) have better effects in both the glucose consumption and the number of cells as compared to the aggregates obtained in Comparative Example 1-1 (E-cadherin-Fc concentration=0 µg/ml). In particular, on Day 5 of the culture, the glucose consumption was about twice higher, and the number of cells was about 1.5 to 1.75 times larger in Example 1-1 compared to those in Comparative Example 1-1. Such a tendency was even stronger in Examples 1-2 to 1-5, wherein the glucose consumption was 2 times higher in Examples 1-2 and 1-5, and 2.5 times higher in Examples 1-3 and 1-4; and the number of cells was about 1.8 times larger in Example 1-2, about 2.5 times larger in Example 1-3, about 3 times larger in Example 1-4, and about 2.3 times larger in Example 1-5, so that it can be seen that a large amount of pluripotent stem cells were obtained. Further, since better results were obtained in Examples 1-2 to 1-4, wherein the diameters of aggregates were more uniformly controlled as shown in FIG. 2, it can be seen that the growth efficiency can be increased by suppressing excessive aggregation of cells to allow formation of more aggregates having appropriate particle sizes. From these results, it can be seen that the obtained cells are stem cells maintaining undifferentiation and pluripotency of differentiation. In general, taking into account the fact that there is a limit in the size to which a cell aggregate can grow depending on dispersion of nutrient substrates and oxygen, control of the diameter of the aggregates is assumed to significantly contribute to simplification of the process of large-scale culture of human iPS cells.

Example 2

Example 2-1

To a 12-well plate subjected to low-cell-adhesion treatment, 1 mL of mTeSR®1 was added, and hiPS cells (TkDN4-M, Stem Cell Bank, The University of Tokyo) (5×10 cells/ml) provided in advance and, as a substance that inhibits a cell adhesion molecule(s) of the hiPS cells, recombinant E-cadherin (hRP-0339, manufactured by LD Biopharma) (10 µg/ml) were added at the same time, followed by performing rotation culture at a speed of 90 rpm for 1 day.

Example 2-2

Aggregates were obtained in the same manner as in Example 2-1 except that a neutralizing antibody against E-cadherin (E-cadherin antibody MAB3199Z, manufactured by Millipore) (16 g/ml) was used as the substance that inhibits a cell adhesion molecule(s) of the hiPS cells in Example 2-2.

Example 2-3

Aggregates were obtained in the same manner as in Example 2-1 except that E-cadherin-Fc (10 µg/ml) was used as the substance that inhibits a cell adhesion molecule(s) of the hiPS cells in Example 2-3.

Comparative Example 2-1

Aggregates were obtained in the same manner as in Example 2-1 except that the recombinant E-cadherin was not used in Comparative Example 2-1.

<Observation of Cell Aggregates>

Figure 5:
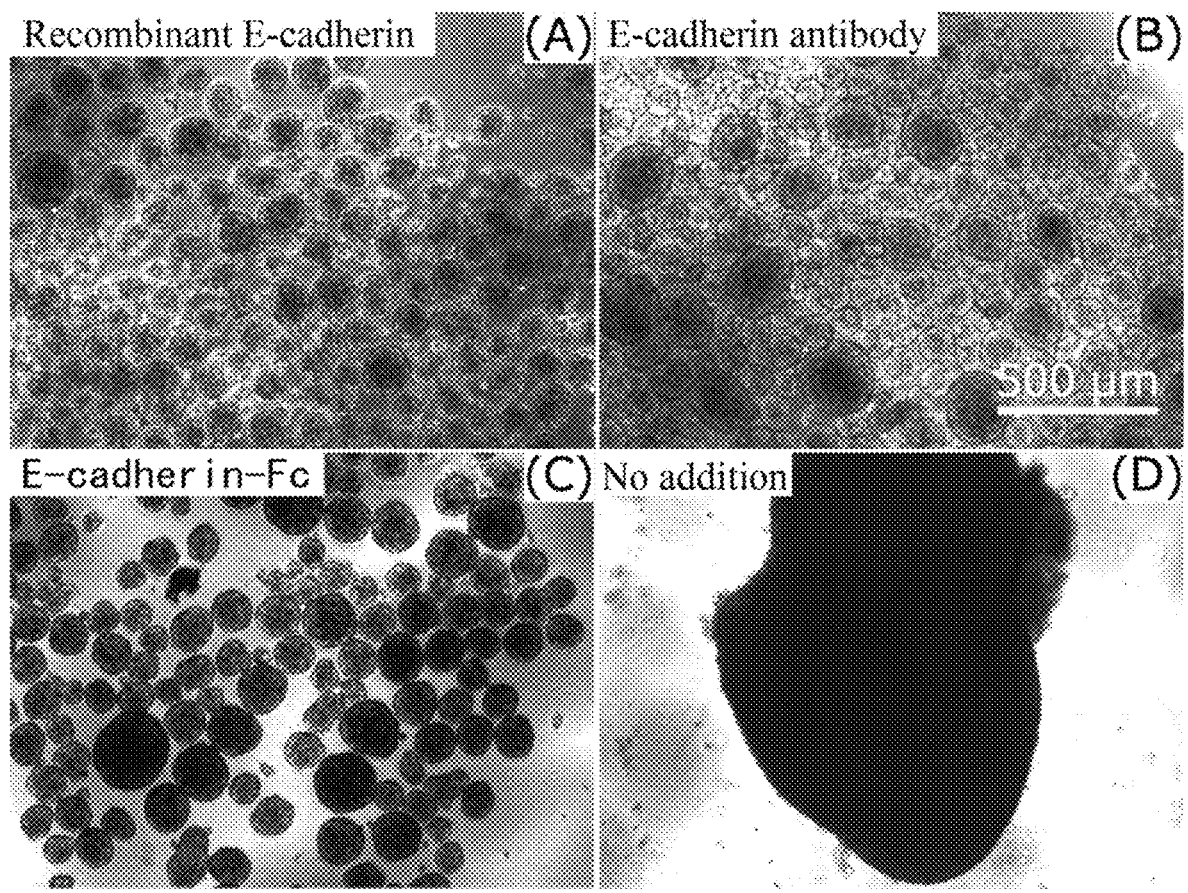
FIG. 5 shows photograph diagrams ((A) to (D)) showing the shapes of aggregates obtained in Examples 2-1 to 2-3 and Comparative Example 2-1, wherein human iPS cells were treated with recombinant E-cadherin (10 μg/ml), E-cadherin antibody (16 μg/ml), or E-cadherin-Fc (10 μg/ml), or without addition of a substance that inhibits a cell adhesion molecule(s), and then subjected to rotation suspension culture for 1 day, which photographs were taken with a phase-contrast microscope. The scale bar represents 500 μm.

Morphology of cell aggregates in Examples 2-1 to 2-3 and Comparative Example 2-1 was observed using a phase-contrast microscope (product name. DM IRB; manufactured by LEICA). The obtained micrographs are shown in FIG. 5 (A) to (D). From FIG. 5 (A) to (D), it can be seen that the aggregates obtained using any of the recombinant E-cadherin, neutralizing antibody against E-cadherin, and E-cadherin-Fc can have more uniformly controlled diameters than the aggregates obtained in Comparative Example 2-1 (without addition of a substance that inhibits a cell adhesion molecule(s)). Moreover, since E-cadherin-Fc produces larger aggregates having more uniform shapes than the recombinant E-cadherin or the neutralizing antibody against E-cadherin, it is assumed that E-cadherin-Fc allows production of aggregates all of which have diameters of not less than 20 µm and less than 1 mm after 48 hours of the culture that are larger than those obtained using the recombinant E-cadherin or the neutralizing antibody against E-cadherin, and also allows production of a larger number of cells.

Example 3

Example 3-1

To a 12-well plate subjected to low-cell-adhesion treatment, 1 mL of Essential 8® was added, and hiPS cells (TkDN4-M, Stem Cell Bank, The University of Tokyo) ($2\times10^5$ cells/ml) provided in advance and, as a substance that inhibits a cell adhesion molecule(s) of the hiPS cells, E-cadherin-Fc (50 µg/ml) were added at the same time, followed by performing rotation culture at a speed of 100 rpm for 5 days. On Day 2 of the culture and thereafter (from 48 hours after the beginning of the culture), medium replacement was carried out every day with a medium to which E-cadherin-Fc was not added.

Example 3-2

Aggregates were obtained in the same manner as in Example 3-2 except that the concentration of E-cadherin-Fc in Example 3-1 was 100 µg/ml.

Comparative Example 3-1

Aggregates were obtained in the same manner as in Example 3-1 except that E-cadherin-Fc was not used in Comparative Example 3-1.

<Observation of Cell Aggregates>

Figure 6:
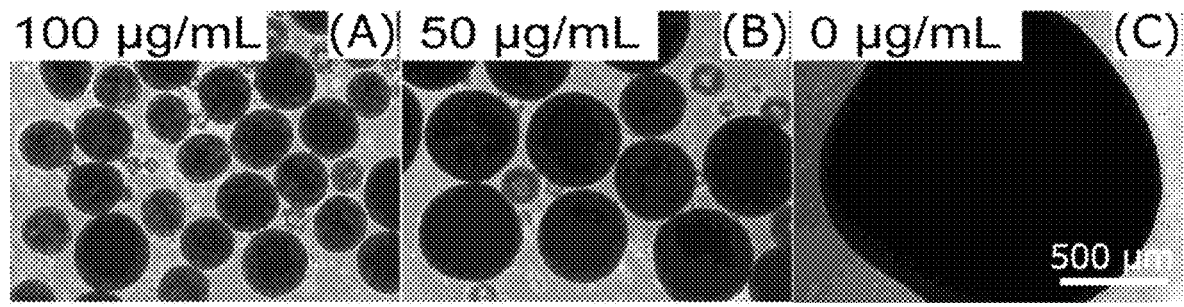
FIG. 6 shows photograph diagrams ((A) to (C)) showing the shapes of aggregates obtained in Examples 3-1 and 3-2, and Comparative Example 3-1, wherein human iPS cells were treated with E-cadherin-Fc in an amount of 0, 50, or 100 μg/ml and then subjected to rotation suspension culture for 2 days, which photographs were taken with a phase-contrast microscope. The scale bar represents 500 μm.
Figure 7:
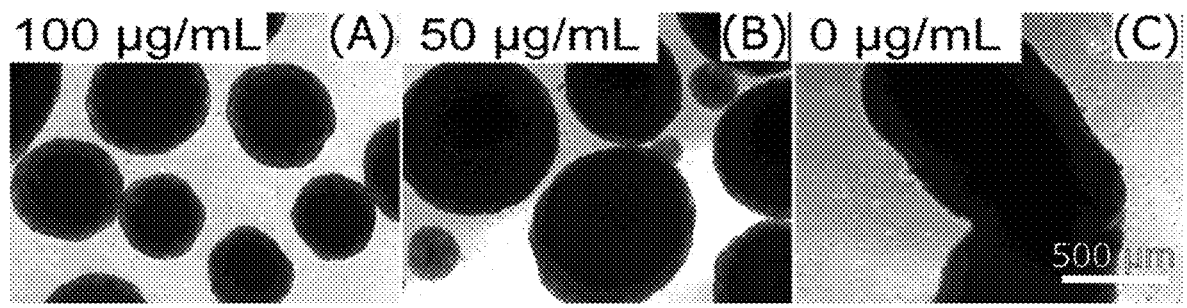
FIG. 7 shows photograph diagrams ((A) to (C)) showing the shapes of aggregates obtained in Examples 3-1 and 3-2, and Comparative Example 3-1, wherein human iPS cells were treated with E-cadherin-Fc in an amount of 0, 50, or 100 μg/ml and then subjected to rotation suspension culture for 5 days, which photographs were taken with a phase-contrast microscope. The scale bar represents 500 μm. The shape of the aggregate in FIG. 7 (C) is thought to be due to deformation during pipetting.

Morphology of cell aggregates in Examples 3-1 and 3-2, and Comparative Example 3-1 on Day 2 and Day 5 of the culture was observed using a phase-contrast microscope (product name, DM IRB; manufactured by LEICA). The obtained micrographs are shown in FIGS. 6 and 7. From the results shown in FIGS. 6 and 7, it can be seen that the size of the aggregates can be controlled also in cases where Essential 8® is used as the medium. On Day 5 of the culture, in the cases where E-cadherin-Fc was added, the size of the aggregates was larger than that on Day 2 of the culture, and the diameter of the aggregates was controlled at about 500 µm.

Here, taking into account Examples 1-1 to 1-5, wherein mTeSR®1 was used as the medium (FIG. 2), it can be seen that use of mTeSR®1, whose protein content is high (protein content, about 18 mg/ml), as the medium produces an effect equivalent to that produced by use of Essential 8®, whose protein content is low (protein content, about 9 µg/ml), even with a smaller amount of the substance that inhibits a cell adhesion molecule(s). This is assumed to be because, when the medium with low protein content was used, adsorption of the substance that inhibits a cell adhesion molecule(s) to other cell membranes and the culture substrate occurred before blocking of the cell membrane cadherin of interest.

<Measurement of Glucose Consumption and Number of Cells>

Figure 8:
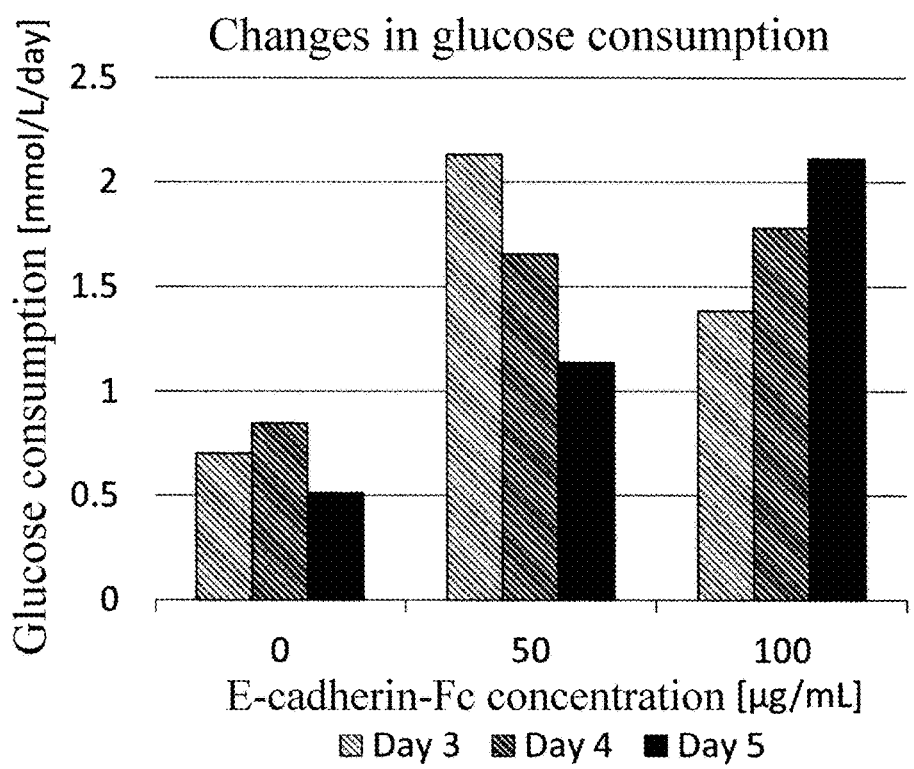
FIG. 8 is a graph diagram showing the glucose consumption of cells as measured for the culture media used in Examples 3-1 and 3-2, and Comparative Example 3-1.
Figure 9:
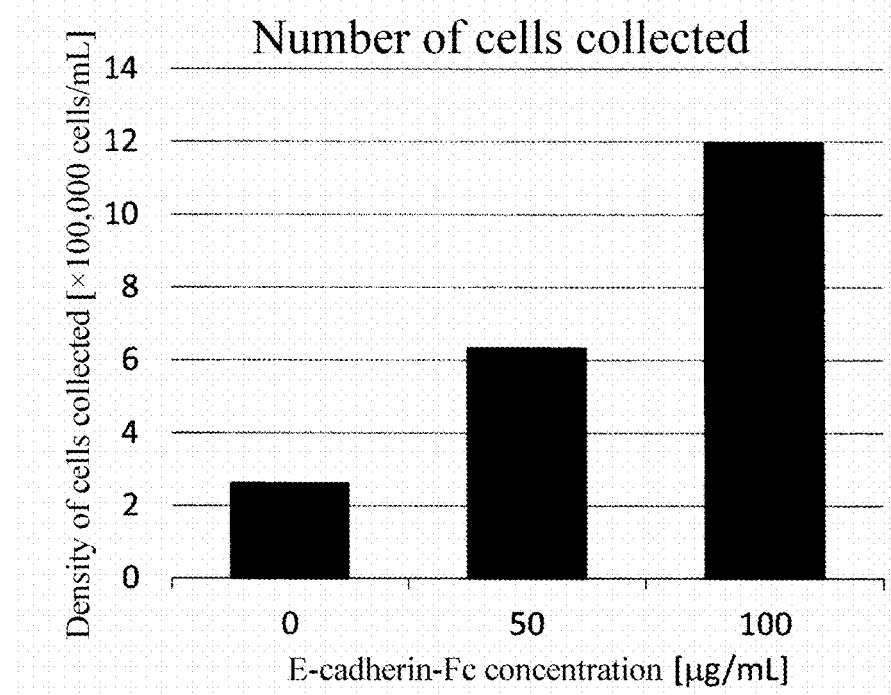
FIG. 9 is a graph diagram showing the densities of cells per 1 ml of medium, which cells were collected after 5 days of culture in Examples 3-1 and 3-2, and Comparative Example 3-1.

As a result of measurement of the glucose consumption and the number of cells for Examples 3-1 and 3-2, and Comparative Example 3-1 in the same manner as described above (FIG. 8 and FIG. 9), it could be confirmed that addition of E-cad-Fc exhibits an excellent effect in both the glucose consumption and the number of cells.

The invention claimed is:

1. A method for culturing cells by suspension culture, said method comprising
controlling cell adhesion by adding a substance that inhibits a cell adhesion molecule(s) of said cells to a medium to control cell aggregation of said cells;
culturing said cells in suspension in the presence of said substance that inhibits a cell adhesion molecule(s) for 24 to 48 hours;
culturing said cells in suspension in the absence of a substance that inhibits a cell adhesion molecule(s) until the sizes of all aggregates are not less than 250 μm and less than 1 mm,
wherein said substance that inhibits a cell adhesion molecule(s) contains a fusion protein comprising a domain exhibiting an amino acid homology of not less than 80% to an extracellular domain of an E-cadherin having an EC1 domain and further comprises an Fc region of an immunoglobulin; and
wherein said substance that inhibits a cell adhesion molecule(s) has an adhesion activity to E cadherin.

2. The culture method according to claim 1, wherein said substance that inhibits a cell adhesion molecule(s) is added to said medium at a concentration of 10 to 50 μg/ml.

3. The culture method according to claim 1, wherein said cells are stem cells or epithelial cells.

4. The culture method according to claim 2, wherein said cells are stem cells or epithelial cells.

5. The culture method according to claim 1, wherein said substance that inhibits a cell adhesion molecule(s) contains a fusion protein comprising a domain exhibiting an amino acid homology of not less than 85% to an extracellular domain of an E-cadherin.

6. The culture method according to claim 1, wherein said substance that inhibits a cell adhesion molecule(s) contains a fusion protein comprising a domain exhibiting an amino acid homology of not less than 90% to an extracellular domain of an E-cadherin.

* * * * *

UNITED STATES PATENT AND TRADEMARK OFFICE
CERTIFICATE OF CORRECTION

PATENT NO. : 11,225,644 B2  
APPLICATION NO. : 15/547316  
DATED : January 18, 2022  
INVENTOR(S) : Yasuyuki Sakai et al.

Page 1 of 1

It is certified that error appears in the above-identified patent and that said Letters Patent is hereby corrected as shown below:

On the Title Page

Please change the Assignees as follows:
From:
"(73) Assignees: SOMAR CORPORATION, TOKYO (JP)
THE UNIVERSITY OF TOKYO, TOKYO (JP)"
To:
--(73) Assignees: THE UNIVERSITY OF TOKYO, TOKYO (JP)
SOMAR CORPORATION, TOKYO (JP)--

Signed and Sealed this  
Sixteenth Day of August, 2022

Katherine Kelly Vidal  
*Director of the United States Patent and Trademark Office*